United States Patent [19]

Suzuki et al.

[11] Patent Number: 4,969,970
[45] Date of Patent: Nov. 13, 1990

[54] APPARATUS FOR PROVIDING SANITARY GOODS WITH ATTACHMENT MEANS WITH RESPECT TO CLOTHING

[75] Inventors: Migaku Suzuki; Masamitsu Yamamoto; Hiroshi Ujimoto; Yoshikazu Tanaka, all of Kawanoe; Hiromi Aono, Ehime, all of Japan

[73] Assignee: Uni-Charm Corporation, Ehime, Japan

[21] Appl. No.: 287,142

[22] Filed: Dec. 21, 1988

Related U.S. Application Data

[63] Continuation of Ser. No. 2,300, Jan. 12, 1987, abandoned.

[30] Foreign Application Priority Data

Oct. 1, 1986 [JP] Japan ................................ 61-3142

[51] Int. Cl.5 ........................ B32B 31/00; B32B 3/10
[52] U.S. Cl. .................................. 156/495; 156/229; 156/252; 156/513; 428/137
[58] Field of Search ............... 156/164, 211, 212, 214, 156/229, 257, 230, 494, 495, 496, 513, 514, 257, 270; 604/369, 378; 428/137, 299, 910

[56] References Cited

U.S. PATENT DOCUMENTS

| 3,183,116 | 5/1965 | Schaay | 156/230 |
| 3,985,599 | 10/1976 | Le Poutre et al. | 156/229 |
| 3,985,600 | 10/1976 | Blais | 156/229 |
| 4,297,154 | 10/1981 | Keller | 156/212 |
| 4,333,782 | 6/1982 | Pieuiak | 156/229 |
| 4,507,163 | 3/1985 | Meuard | 156/229 |
| 4,525,229 | 6/1985 | Suzuki et al. | 156/164 |
| 4,534,769 | 8/1985 | DeJoukheer et al. | 604/369 |
| 4,560,372 | 5/1984 | Pieuiak | 156/229 |
| 4,596,568 | 6/1988 | Flug | 604/378 |
| 4,637,819 | 1/1987 | Quellette et al. | 604/369 |
| 4,692,368 | 9/1987 | Taylor et al. | 156/264 |

Primary Examiner—Michael W. Ball
Assistant Examiner—Louis Falasco
Attorney, Agent, or Firm—Fred Philpitt

[57] ABSTRACT

An apparatus for modifying and joining a sheet of foam to a non-elastic component that includes slitting the foam to form a plurality of openings, forming the slit foam into a U shaped slack condition and joining surfaces of the foam sheet to a non-elastic component adhering the two together.

3 Claims, 4 Drawing Sheets

APPARATUS FOR PROVIDING SANITARY GOODS WITH ATTACHMENT MEANS WITH RESPECT TO CLOTHING

This is a continuation of application Ser. No. 2,300, filed Jan. 12, 1987 now abandoned.

DETAILED DESCRIPTION OF INVENTION

1. Field of the Invention

The present invention relates to method and apparatus for providing sanitary goods with attachment means with respect to clothing and more particularly to method and apparatus for providing said goods such as sanitary napkin and hemorrhoidal pad with means by which said goods can be attached to underclothing so that, even when it is unsuitable or difficult to fix said goods directly to user's body, the surface of said goods to be in contact with the user's skin may be held at a desired position in contact with the user's skin.

2. Prior Art

Sanitary goods such as sanitary napkin provided on its surface to be out of contact with the user's skin with adhesive applied thereon as attachment means with respect to underclothing are well known. As the other attachment means, a plastic foam sheet having a high frictional resistance relative to underclothing joined to said surface to be out of contact with the user's skin is also known. However, no prior art concerning the method and the apparatus according to the present invention has been disclosed, so far as the inventors have been informed.

Problems to be solved according to the present invention

As will be described in detail later, the present invention resides in provision of attachment means for sanitary goods with clothing by applying adhesive onto a surface of the sanitary goods to be brought into contact with the user's skin and integrally joining a soft, elastic plastic foam sheet formed with a plurality of openings to said surface. Although formation of such plurality of openings through the plastic foam sheet might be tried by punching or needling, with the punching technique, it will be difficult to form an opening of a diameter larger than 1 mm, since the plastic foam sheet is elastically extendable and, with said needling technique, it is difficult to achieve a desired workability and a desired working rate because of the same reason as in the case of said punching technique.

A principal object of the present invention is, in view of such aspect, to provide method and apparatus for effectively providing sanitary goods with said attachment means and thereby to solve the above-mentioned problems.

The other objects of the present invention will be apparent from following description With the method and the apparatus according to the present invention, it is possible to eliminate the inconveniences which have been inevitable, as mentioned above, in the well known attachment means relying on adhesive, on one side, and the well known attachment means relying on the plastic foam sheet, on the other hand, and to obtain attachment means of sanitary goods maintaining the advantages of these will known attachment means. More specifically, in the case of sanitary napkin, for example, adhesive has conventionally been applied onto a limited area of the napkin in view of a fact that application of adhesive onto a larger area would stain underclothing over a correspondingly larger area with adhesive and often deteriorate underclothing itself. However, after the user has worn such sanitary napkin for a relatively long time or the user has done a relatively active motion, a rest area not fastened to underclothing would displace or deform. In the case of sanitary napkin having the soft, elastic plastic form sheet joined thereto as attachment means, on the other hand, attachment function of said form sheet relying on a frictional resistance would be insufficient relative to underclothing unless said foam sheet is kept against underclothing under a relatively high pressure. Furthermore, such foam sheet has no attachment function in the direction away from underclothing, so that, when the underclothing is slipped down, the sanitary napkin might often accidentally fall off and stain other clothes or floor with menstruum contained in said napkin. Nevertheless, adhesive force of said adhesive and frictional resistance of said foam sheet may be effectively utilized in combination so as to eliminate the disadvantages of these two to obtain a novel attachment means which can never be obtained from the former or the latter alone. The present invention resides in a method for providing sanitary goods with such attachment means.

Measures to solve problems

To solve the above-mentioned problems, the present invention provides method and apparatus for providing sanitary goods with attachment means with respect to clothing comprising steps and means as set forth.

Method: intermittently forming transversely elongate slits at given intervals both longitudinally and transversely of a continuous, soft and elastic plastic foam sheet as the latter is delivered from a roll thereof; forming openings by stretching said foam sheet provided with said slits longitudinally at a given percentage so as to open said slits; rolling said foam sheet formed with said openings as said foam sheet is kept in said stretched state; leaving said rolled foam sheet for a given period so that said foam sheet obtains permanent elongation set of a given percentage; transporting said foam sheet having obtained said permanent elongation set, after said foam sheet has been delivered and contracted to said permanent elongation set, to a later step of joining said foam sheet to a continuous component substantially non-elastic and forming at least a part of said goods, under a tension causing neither warps nor wrinkles in said goods due to contraction of said foam sheet; transporting said component of said goods to said step of joining; applying adhesive onto one side of any one of said foam sheet and said component of said goods prior to said joining step; and forming continuous goods by integrally joining said foam sheet and said component of said goods with interposition of said adhesive during said joining step.

Apparatus: various means corresponding to said respective steps.

Said continuous goods constructed according to said method and apparatus may be final product, depending on the kinds of said goods, as in a continuous condition or after cut into individual product of a predetermined length. It will be readily understood that the former may be in such a form that the user can cut an individual unit apart from the rest or cut this continuous goods into a desired length for actual use. In either case, the former is relatively thin so that this may be folded into a non-bulky layers or rolled into a compact package.

The latter, on the contrary, is that which must be previously separated from one another into individual product from viewpoints of its use and/or of packaging.

The present invention will be described more in detail, by way of example, in reference with the accompanying drawing which illustrates preferred embodiments.

| | |
|---|---|
| 1 | foam sheet |
| 1a | U-shaped slack |
| b | slitter roller |
| 12, 13, 14, 15 | draft rollers |
| 16 | openings |
| 22 | independent drive roller |
| 23 | constant velocity roller |
| 25a, 25b, 26a, 26b, 27a, 27b | detector means |
| 34 | backsheet of sanitary napkin |
| 40 | first applicator means |
| 47 | second applicator means |
| 53 | other component of sanitary napkin |
| 55 | sanitary napkin |
| 56 | first adhesive |
| 57 | second adhesive |

Figure 1:
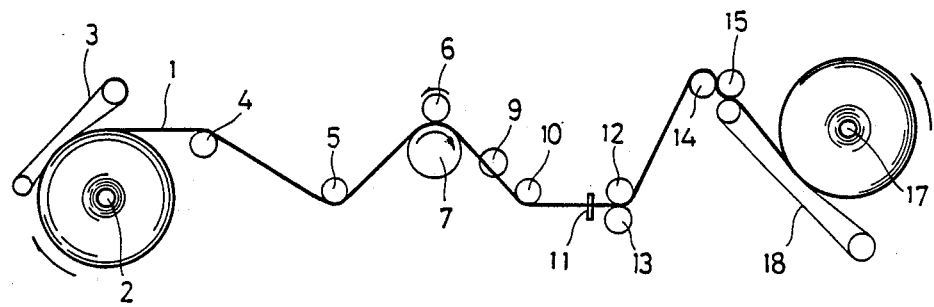
FIG. 1 is a schematic side view illustrating a process in which a wide foam sheet stored around a roll is provided with slits, then stretched to form openings and taken up around another roll, using an apparatus according to the present invention.
Figure 2:
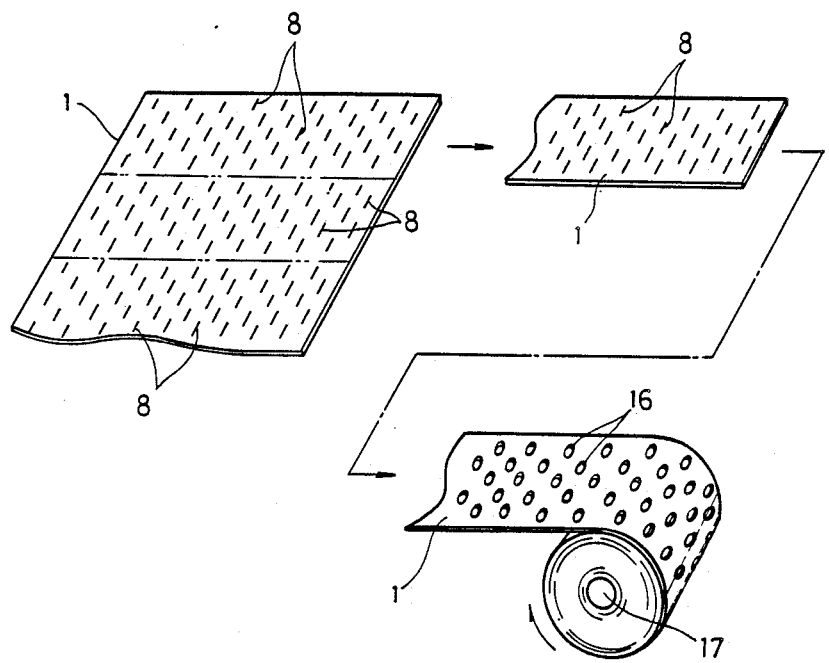
FIG. 2 is a partial perspective view showing a manner in which the slits are formed in said foam sheet and then opened to form said openings.

Referring to FIG. 1, a wide, soft and elastic continuous polyurethane foam sheet 1 is stored around a roll 2. The foam sheet 1 is delivered from the roll under a light pressure exerted by a touch belt 3 on its surface, transported via guide rollers 4, 5 between a slitter roller 6 having a plurality of knife edges at predetermined intervals around its peripheral surface and a counter roller 7 and thereby transversely elongate slits 8 are intermittently and formed at predetermined intervals both longitudinally and transversely of the foam sheet, as shown by FIG. 2. The wide foam sheet 1 thus formed of the slits 8 is then cut by a cutter roller 9 into a desired width. Each narrow foam sheet thus cut into the predetermined width is now transported via a guide roller 10 to a subsequent step. Although FIG. 2 illustrates a single narrow foam sheet transported to said subsequent step, the wide foam sheet 1 is really cut into a predetermined number of such narrow foam sheets at predetermined intervals and the respective narrow sheets thus cut are transported via a separator guide 11 to the subsequent step, respectively. It should be noted here that, in a following description, a single narrow foam sheet will be considered and referred to simply as the foam sheet 1.

The foam sheet 1 is stretched under influence of a differential velocity between a pair of draft rollers 12, 13 and another pair of draft rollers 14, 15 operating at a circumferential velocity higher than that of the former pair to open the slits 8, as seen in FIG. 2, so as to form substantially oval or circular openings 16. The foam sheet 1 thus formed with the openings 16 is now taken up around a take-up roll 17 as said foam sheet 1 is maintained in said stretched condition and under a light pressure exerted by a touch belt 18 on its surface.

The foam sheet 1 thus taken-up is left in such taken-up state for a predetermined period so that the openings 16 are maintained each in a predetermined size and said foam sheet 1 obtains elongation set (referred to hereinafter as permanent elongation set) of a predetermined percentage selected so that neither warps nor wrinkles occur in sanitary goods due to a contracting force of the foam sheet 1 after said foam sheet 1 has been joined to said sanitary goods.

Such permanent elongation set will be described more in detail. The foam sheet 1 as a component constituting the attachment means of the sanitary goods with respect to clothing preferably has a thickness of 0.8 to 3 mm and a stiffness of 5 to 20 Kg/314 $cm^2$ (according to JIS-K6401) prior to being stretched and a thickness of 0.5 to 2.5 mm with each opening 16 having a diameter of 1 to 10 mm and a transverse and longitudinal arrangement pitch of 3 to 30 mm after having been stretched. To provide the openings with such diameter and such arrangement pitch, it is required that the slit should be 1.5 to 15 mm long and arranged at a pitch of 2 to 20 mm both longitudinally and transversely of the foam sheet 1. To obtain the foam sheet 1 in such condition, a stretch percentage of the foam sheet 1 is preferably 110 to 150% when taken up and said permanent elongation set is preferably 105 to 145%. Experiments conducted by the inventors have indicated that a foam sheet with a thickness of 0.8 to 3 mm, a stiffness of 5 to 20 Kg/314 $cm^2$, a slit length of 1.5 to 15 mm and a longitudinal and transverse arrangement pitch of the slits of 2 to 20 mm ("STAYWHITE ESW" available from INOUE M. T. P. Co. Ltd., Japan) may be stretched by 110 to 150%, taken up with said stretch percentage being maintained and left in this condition for 6 days or longer to provide said permanent elongation set. With a stretch percentage less than 110%, not only said permanent elongation percentage can not be achieved but also the slits 8 can not be adequately opened to form the desired openings 16 and, with a stretch percentage of 150% or higher, cells located along the surface of the foam sheet 1 collapse, resulting in an insufficient frictional resistance and the openings 16 remain elongate longitudinally thereof almost as if they remain closed.

Figure 3:
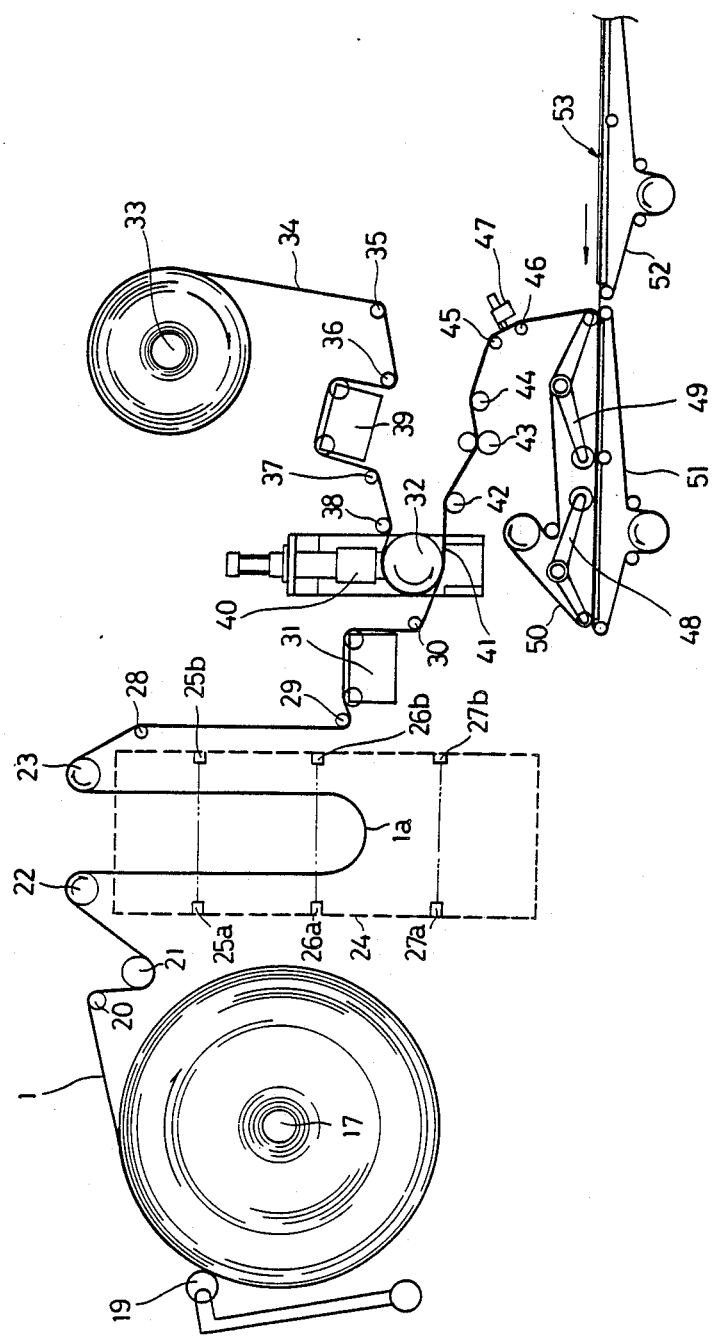
FIG. 3 is a schematic side view illustrating a process in which said foam sheet formed with said openings is joined to sanitary goods, using another apparatus according to the present invention.

Referring to FIG. 3, the foam sheet 1 thus taken up and provided with the permanent elongation set is delivered and subjected to the steps for incorporation into the sanitary goods, i.e., the sanitary napkin in this embodiment. The foam sheet 1 taken up around the roll is delivered under a light pressure exerted by a touch roller 19 on its surface and guided via guide rollers 20, 21 into a free zone box 24. Above the box 24, there is provided at the inlet side an independent drive roller 22 adapted to be controlled by a DC motor operating separately of a drive system serving to drive a transporation line of the foam sheet 1 and there is provided at the outlet side opposed to said inlet side a constant velocity roller 23 operatively associated with the drive system for said transportion line. The foam sheet 1 always slacks in U-shape within the box 24 and thereby contracts to said permanent elongation set.

Figure 4A:
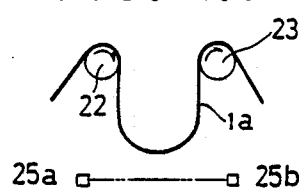
FIGS. 4A, 4B and 4C are diagrams illustrating a relative position of U-shaped slack of said foam sheet and detector means within a free zone in which said foam sheet is partially slacked in the U-shaped during transport of said foam sheet to a step for joining said foam sheet to said sanitary goods.
Figure 4B:
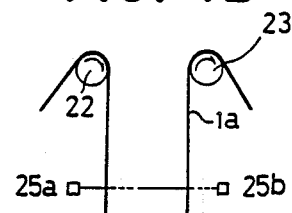
Figure 4C:
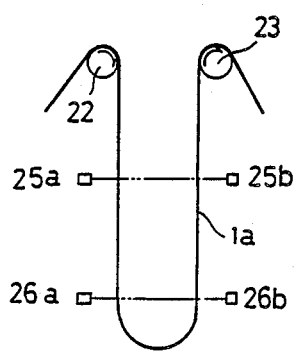

A construction within the box 24 will be described in reference with FIG. 4. Below the independent drive roller 22 and the constant velocity roller 23, there are provided, vertically at predetermined intervals and horizontally in opposition to one another, first means 25a, 25b, second means 26a, 26b and third means 27a, 27b serving to control the DC motor of said independent drive roller 22, of which the reference numerals 25a, 26a and 27a designate irradiation sources while the reference numerals 25b, 26b and 27b designate light receivers such as photoelectic tuves. As will be seen in FIG. 4A, when the foam sheet 1 is not interposed between the irradiation source 25a and the corresponding light receiver 25b so as to conduct a light beam therebetween, a detection signal based on a light input coming from said light receiver 25b controls the DC motor of the independent drive roller 22 so that the latter operates at a r.p.m. higher than that of the constant velocity roller 23 and, in consequence, a U-shaped slack 1a is formed. When the U-shaped slack 1a is interposed between the irradiation source 25a and the corresponding light receiver 25b so as to interrupt any light beam conducted therebetween but not interposed between the irradiation source 26a and the corresponding light receiver 26b so as to conduct a light beam therebetween, as shown in FIG. 4B, a detection signal based on a light input coming from said light receiver 26b controls the DC motor of the independent drive roller 22 so that the latter operates at a r.p.m. higher than that of the constant velocity roller 23 and, in consequence, the U-shaped slack 1a is further lowered. When the U-shaped slack 1a is interposed between the irradiation sources 25a, 26a and the corresponding light receivers 25b, 26b so as to interrupt any light beams conducted between these associated irradiation sources and light receivers, respectively, as shown in FIG. 4C, the DC motor is controlled so that the independent drive roller 22 operates at a r.p.m. substantially same as that of the constant velocity roller 23. Normally, the conditions of the U-shaped slack 1a as shown by FIGS. 4B and 4C are repeated. When there occurs something abnormal, for example, when the drive system for the transport line of the foam sheet 1 is rapidly accelerated and, with consequence, the r.p.m. of the independent roller 22 has become lower than that of the constant velocity roller 23, the DC motor of said independent drive roller 22 is controlled so that the latter has its r.p.m. rapidly become higher than that of said constant velocity roller 23. On the contrary, when the U-shaped slack 1a is interposed between the irradiation source 27a and the corresponding light receiver 27b so as to interrupt any light beam conducted therebetween, the DC motor of said independent drive roller 22 is controlled so that the latter is stopped until the U-shaped slack 1a is lifted from between the irradiation source 27a and the corresponding light receiver 27b and said normal condition is restored.

The foam sheet 1 is thus slacked in U-shape and thereby contracted to said permanent elongation set for a purpose as follows. A certain degree of tension under which the foam sheet 1 is transported to a subsequent step for joining the foam sheet 1 with the sanitary goods or a component thereof is essential. However, a stretch higher than said certain degree of tension in addition to said stretch of 110 to 150% which has already been involved in the foam sheet 1 for said taking up would disadvantageously result in formation of warps and wrinkles in the sanitary napkin so far as said foam sheet 1 is joined to said sanitary napkin under such excessive tension.

Experiments conducted by the inventors have shown that, with the foam sheet 1 meeting the above-mentioned requirements and with the sanitary napkin having the stiffness substantially same as that of the napkin commonly used in practice, none of said inconveniences occurs even when the foam sheet 1 is placed under a tension corresponding to a sum of said permanent elongation set of 105 to 145% and an additional stretch less than 10%. Based on this knowledge, the foam sheet 1 is transported under a tension such that said additional stretch may be kept less than 10% and the foam sheet 1 may be transported still under a proper control, via guide rollers 28, 29, 30 and means 31 for prevention of zigzag movement to a first joining step for joining the foam sheet 1 to a backsheet as a component of the sanitary napkin. Said first joining step includes a support roller 32 along the underside of which the foam sheet 1 is transported.

A continuous backsheet 34 being a component of the sanitary napkin and stored around a take-up roll 33 is delivered and transported via guide rollers 35, 36, 37, 38 and means 39 for prevention of zigzag movement to the support roller 32. Applicator means 40 located above said support roller 32 applies first adhesive onto one side of the backsheet 34 as the latter travels along said support roller 32 from its upper side towards its lower side. In said first joining step, the foam sheet 1 is joined integrally to the backsheet 34 with interposition of said first adhesive to form a composite sheet 41. The composite sheet 41 is transported to second joining step for joining this composite sheet to another continuous member forming another component of the sanitary napkin via guide rollers 42, 43, 44, 45, 46 and, in the course of such transport, applicator means 47 located between the guide rollers 45 and 46 applies second adhesive onto the other side of the backsheet 34.

Said second joining step includes a belt conveyor 50 provided with means 48, 49 adapted to resiliently press against this belt conveyor 50 and another belt conveyor 51 opposed to said belt conveyor 50 so that the composite sheet 41 may be transported between these belt conveyors 50, 51. Said other continuous member 53 as the other component of the sanitary napkin is transported by the belt conveyor 52 to said second joining step. Thus, the composite sheet 41 is joined in said second joining step intergrally to the continuous member 53 with interposition of said second adhesive to form the sanitary napkin The sanitary napkin thus constructed is then transported to the subsequent step (not shown) to be cut into a predetermined length.

Figure 5:
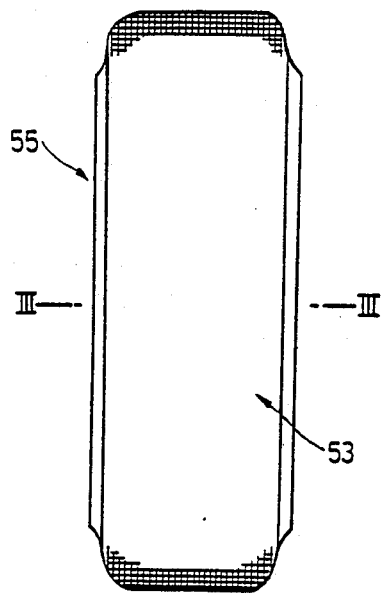
FIG. 5 is a front view of an individual sanitary napkin as an example of the sanitary goods provided by said apparatus with attachment means.
Figure 6:
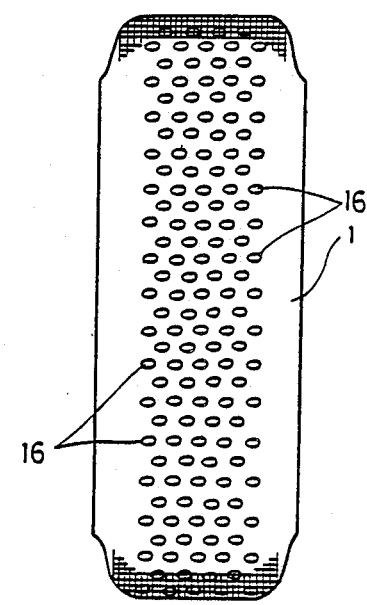
FIG. 6 is a rear view thereof.
Figure 7:
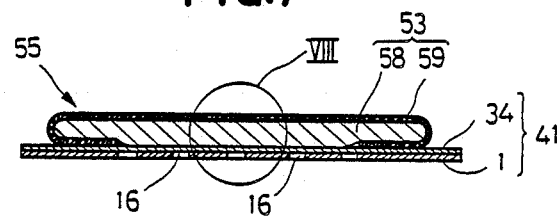
FIG. 7 is a section taken along a line VII—VII in FIG. 5.
Figure 8:
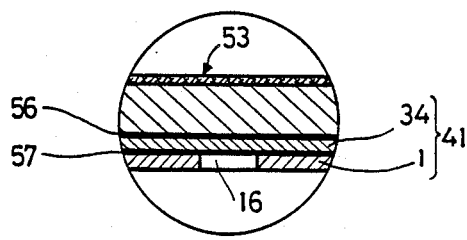
FIG. 8 is an enlarged view of an encircled portion.

Referring to FIGS. 5 and 6, reference numeral 55 designates such sanitary napkin finished by said cutting step and reference numerals 56, 57 designate said first and second adhesives, respectively. The component 53 of the sanitary napkin comprises an absorbent 58 and a topsheet 59. Namely, the sanitary napkin 55 comprises adhesive 57 applied onto the backsheet 34 defining the surface adapted to be out of contact with the user's skin and the foam sheet 1 joined thereto, and is constructed so that the adhesive 57 is partially exposed through the openings 16. Water-impermeable material, for example, plastic film is used as the backsheet 34, absorptive material, for example, crushed pulp is used as the absorbent 58 and water-permeable material, for example, nonwoven fabric is used as the topsheet 59, as in the sanitary napkin of prior art. In use of such sanitary napkin 55, said napkin 55 is attached to underclothing with the foam sheet 1 downwardly facing said underclothing and being depressed thereagainst. Once attached, the sanitary napkin 55 is held by means of adhesive 57 exposed through the openings 16 and adhering to underclothing against any displacement in the direction in which the sanitary napkin might be peeled off from the corresponding surface area of underclothing and also prevented under effects of the adhesive force and the frictional resistance of the foam sheet 1 relative to underclothing from being displaced in the direction in which the sanitary napkin 55 tends to move relative to the corresponding surface are of underclothing. Said application thickness of the adhesive 57 onto the backsheet 34 is preferably 15 to 350 μ in order to obtain the desired effect of said adhesive 57.

Although the present invention has been described according to the embodiment adapted to provide the sanitary napkin 55 with the attachment means comprising the foam sheet 1 formed with the openings 16 and the adhesive 57, the object to be provided with such attachment means may be other continuous sanitary goods to be used after cut off into a suitable length. Referring to FIG. 3, the step of delivering the backsheet 34 and the step of joining the foam sheet 1 to the backsheet 34 may be eliminated so that the sanitary goods 53 including the backsheet 34 previously joined thereto is transported by the belt conveyor 52 and then joined to the foam sheet 1. It is also possible to apply onto one side of the form sheet the adhesive by which said foam sheet 1 is joined to the sanitary goods or the component thereof. Although not illustrated, the foam sheet 1 may be previously formed narrower than the surface of the sanitary goods to be out of contact with the user's skin may be suitably trimmed immediately before joined to the sanitary goods or the component thereof. It will be readily achieved by those skilled in the art to construct the apparatus so that the foam sheet 1 is trimmed immediately before joined to said sanitary goods or the component thereof.

EXAMPLE

Initially, the apparatus shown by FIG. 1 was used. A continuous polyurethane foam sheet with a thickness of 1 mm, a width of 1300 mm and a stiffness of 10 Kg/314 cm$^2$ stored around a take-up roll was provided along its entire length with slits at a longitudinal pitch of 6 mm and a transverse pitch of 4 mm. This foam sheet was then longitudinally cut at intervals of 110 mm into narrower foam sheets each of which was taken up as said foam sheet was stretched at a stretch percentage of 130%. As a result of such stretching, said slits were opened to form openings each being oval shape defined by a diameter of 2.5 mm longitudinally and another diameter of 2.8 mm transversely with respect to said foam sheet, respectively. In this condition, the width of said foam sheet had been reduced to 95 mm. Said foam sheet thus formed with the openings was taken up and left taken up for seven days, resulting in a permanent elongation set of 130 % was established in the foam sheet.

Then, the apparatus shown by FIG. 3 was used. Said foam sheet thus having obtained said permanent elongation set was delivered and left to contract to said permanent elongation set, and then fed under a tension corresponding to a stretch percentage of 5 % to the step for joining the foam sheet to the backsheet of the sanitary napkin. At the same time, the continuous backsheet (polyethylene film) 20 μ thick and 95 mm wide was fed from its associated roll to said joining step and in the course of such feed one side thereof was applied with adhesive of hot melt type ("DURO-TAK" available from KANEBO N. N. C. Co. Ltd., Japan) with a thickness of 30 μ so that this continuous backsheet may be joined integrally to said foam sheet to form the continuous composite sheet. Thereafter, the adhesive of an effectiveness same as the first-mentioned adhesive was applied onto the other side of said backsheet with a thickness of 30 μ and simultaneously said composite sheet was joined integrally to the other continuous member constituting the sanitary napkin to form the continuous sanitary napkin. This was cut off into a predetermined length, forming the individual sanitary napkin as shown in FIGS. 5 through 8.

The sanitary napkin was free from said warps and wrinkles due to a contracting force of said foam sheet and presented a desired attachment function with to underclothing.

Effect of invention

The method and apparatus constructed according to the present invention as has been described hereinabove provide the attachment means with respect to clothing which can present the attachment function substantially superior to those of prior art relying on any one of adhesive and plastic foam sheet.

The most important feature of the method and apparatus according to the present invention lies in that said openings are formed in the foam sheet by providing said foam sheet with the slits elongate transversely of said foam sheet and then by stretching said foam sheet longitudinally at a predetermined percentage, so that the workability and the working speed of the openings can be improved. In addition, said foam sheet formed with said openings is left for a predetermined period in said stretched condition to give the foam sheet a permanent elongation set so that said openings can be maintained at predetermined size and shape. Said foam sheet formed with the openings and thus given the permanent elongation set is transported to said joining step under a tension corresponding to the stretch percentage such that neither wrinkles nor warps occur in the sanitary goods du to the contracting force of said foam sheet after said foam sheet has been joined to the sanitary goods or the component thereof in said joining step.

What is claimed is:

1. An apparatus for modifying and joining a sheet of soft and elastic foam, said apparatus comprising:
   (a) transporting means for transporting said foam sheet in a selected transport direction,
   (b) slitter means for forming a plurality of spaced apart elongated slits in said foam, said slits being transverse to said selected transport direction,
   (c) stretching means for forming openings in said slitted foam by stretching said slitted foam sheet between 110% and 115% in a direction transverse to the longitudinal direction of said slits, (d) retainer means for retaining said foam sheet containing said formed openings in a stretched state until said foam sheet and its formed openings achieve a permanent elongation set, (e) a contracting chamber containing sufficient space so that the sheet of foam may be passed therethrough in a U-shaped slack condition, (f) control means to move said foam sheet from said retainer means into and out of said contracting chamber while maintaining the foam sheet in a U-shaped slack condition, (g) joining means for joining one surface of the foam sheet leaving the contracting chamber to one surface of a non-elastic component, and (h) adhesive application means for applying adhesive so that it will be present between the adjoining surfaces of the foam sheet and the non-elastic component.

2. An apparatus according to claim 1 wherein said contracting chamber includes detector means to detect changes in the position of the U-shaped slack of foam sheet therein, said detector means being operatively connected to said control means (f).

3. An apparatus according to claim 1 wherein said slitter means (b) is sized to produce slits in the foam which are 1:5–15 mm long.

* * * * *